United States Patent [19]

Foguet et al.

[11] Patent Number: 4,600,780

[45] Date of Patent: Jul. 15, 1986

[54] N-CYANO-FORMAMIDINES

[75] Inventors: Rafael Foguet; Luis Anglada; Manuel M. Raga; José A. Ortiz; Aurelio Sacristän; José M. Castelló, all of Barcelona, Spain

[73] Assignee: Ferrer International, S.A., Barcelona, Spain

[21] Appl. No.: 595,662

[22] Filed: Mar. 20, 1984

[30] Foreign Application Priority Data

Mar. 30, 1983 [ES] Spain ................................ 521588

[51] Int. Cl.$^4$ .................. C07D 277/20; C07D 211/18
[52] U.S. Cl. ..................................... 548/193; 546/229; 546/230; 548/342; 549/492; 514/927
[58] Field of Search ............... 546/229, 230; 548/191, 548/193, 342, 341, 344; 549/491, 492, 497

[56] References Cited

U.S. PATENT DOCUMENTS 4,252,819 2/1981 Hirata .................................. 549/491
4,309,433 1/1982 Hirai .................................. 549/491

OTHER PUBLICATIONS

Receptors Mediating Some Actions of Histamine by A. S. F. Ash and H. O. Schild, pp. 427–439, (1966).
N-cyanoimidates by K. R. Huffmann and F. C. Schaffer, (1963).
Definition and Antagonism of Histamine H$_2$-Receptors by J. W. Black, et al.

Primary Examiner—Christopher A. Henderson
Attorney, Agent, or Firm—Michael J. Striker

[57] ABSTRACT

New N-cyano-formamidine are disclosed of the formula I:

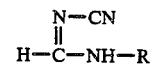

wherein R is 2-[[(5-methyl-1H-Imidazol-4-yl)methyl]-thio]ethyl, 2-[[[5-[dimethylamino)methyl]-2-furanyl]-methyl]thio]ethyl, 2-[[[2-[(aminoiminomethyl)amino]-4-thiazolyl]methyl]thio]ethyl or 3-[3-(1-piperidinylmethyl)phenoxy]propyl, as well as a process for its production, and pharmaceutical preparations containing the same. The compounds possess histamine—induced gastric acid secretion—inhibiting activity, and are indicated for use in the treatment of peptic ulcer and other pathologies caused or stimulated by gastric acidity.

5 Claims, No Drawings

N-CYANO-FORMAMIDINES

BACKGROUND OF THE INVENTION

The present invention relates to the preparation of new N-cyano-formamidines having the formula I:

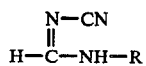
I wherein R is 2-[[(5-methyl-1H-imidazol-4-yl)methyl]-thio]ethyl, 2-[[[5-(dimethylamino)methyl]-2-furanyl]-methyl]thio]ethyl, 2-[[[2-[(aminoiminomethyl)amino]-4-thiazolyl]methyl]thio]ethyl or 3-[3-(1-piperidinylmethyl)phenoxy]propyl, as well as the non-toxic addition salts such as hydrochloride, dihydrochloride and acid maleate.

The compounds of the present invention may be obtained in accordance with the following reaction:

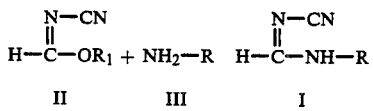

wherein R is as defined above and $R_1$ is a linear or branched alkyl group having 4 carbon atoms at most, preferably ethyl.

The reaction is carried out at room temperature in a medium selected from acetonitrile or an alkanol having 1 to 4 carbon atoms, preferably ethanol. When the amines of the formula III are not used in free form but salified with mineral acids, such as the hydrochlorides or dihydrochlorides, it is convenient before starting reaction with N-cyano-formimidate (II) to neutralize the acid by addition of either an organic base, preferably triethylamine, or an aqueous solution of alkaline or alkaline-earth carbonate or bicarbonate, preferably potassium carbonate.

It is known that histamine, a physiological compound which is found in living organisms, may be bound to certain specific receptors for exerting its activity. Two classes of histamine receptors have been identified so far: $H_1$-receptor (Ash and Schild: Brit. J. Pharmac., 20, 427, 1966), in which histamine activity is blocked by the conventional antihistaminic drugs like mepyramine; and $H_2$-receptor (Black et al., Nature, 236, 385, 1972) in which histamine activity is blocked by cimetidine. The blockade of histamine activity over $H_2$-receptors results in the inhibition of gastric acid secretion, thus making the compounds with this potency effective for the treatment of peptic ulcers and other pathologies causes by or stimulated by gastric acidity.

SUMMARY OF THE INVENTION

It has been found that the compounds of the present invention are remarkably capable of antagonizing histamine $H_2$-receptors, with an acceptable toxicity that makes them therapeutically useful as acid secretion inhibitors.

The novel features which are considered as characteristic for the invention are set forth in particular in the appended claims. The invention itself, however, both as to its construction and its method of operation, together with additional objects and advantages thereof, will be best understood from the following description of specific embodiments.

DESCRIPTION OF THE PREFERRED EMBODIMENTS

The following examples show preparation of the compounds according to the present invention.

EXAMPLE 1

N-cyano-N'-[2-[[(5-methyl-1H-imidazol-4-yl)methyl]-thio]ethyl]formamidine dihydrochloride

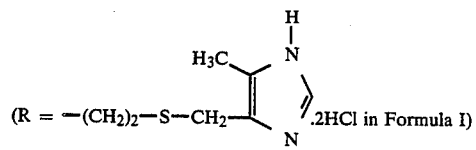

To a solution of 4.88 g of 2-[[(5-methyl-1H-imidazol-4-yl)methyl]thio]ethanamine (prepared according to British Pat. No. 1,338,169 which is hereby incorporated by reference,) in 75 ml of absolute ethanol, are added 5.55 ml of triethylamine. Then 1.96 g of ethyl N-cyano-formimidate in 15 ml of ethanol are added dropwise under stirring and at room temperature (prepared according to Huffman and Schaefer "J.Org.Chem.",28, 1816, 1963). Stirring is continued for 1 hour, after which are added 2.5 ml of 8N HCl/ethanol. A white solid is separated, which is subsequently crystallized in ethanol, filtered off and dried in a vacuum dessicator in the presence of phosphorus pentoxide and sodium hydroxide. 2.9 g of N-cyano-N'-[2-[[(5-methyl-1H-imidazol-4-yl)methyl]thio]ethyl]formamidine are obtained.

Melting point: 168°–170° C.

Elemental analysis: found (C 40.89 H 5.48 N 25.7); calculated (C 41.62 H 5.39 N 26.47).

Sulfur (Schöniger): found 12.34: calculated 12.34.

Chlorides: found 14.6: calculated 13.68.

IR Spectrum: characteristic bands at 2190 cm$^{-1}$ (—C≡N st) and 1615 cm$^{-1}$ (—C=N st).

EXAMPLE 2

N-cyano-N'-[2-[[[5-[(dimethylamino)methyl]-2-furanyl]methyl]thio]ethyl]formamidine

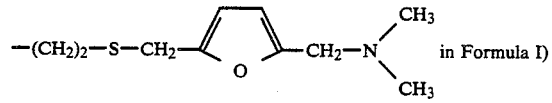

To a solution of 5.6 g of 5-[[(2-aminoethyl)thio]methyl]N,N-dimethylfuranmethanamine (prepared according to Belgian Pat. No. 857,388, hereby incorporated by reference) in 35 ml of acetonitrile are added dropwise 2.56 g of N-cyano-formimidate in 15 ml of acetonitrile, under cooling at 0° C. The mixture is maintained under stirring for 30 minutes and the acetonitrile is removed by vacuum evaporation. A solid residue is formed, which is crystallized from ethyl acetate. 2.1 g are obtained of N-cyano-N'-[2-[[[5-[(dimethyl-amino)-methyl]-2-furanyl]methyl]thio]ethyl]formamidine.

Melting point: 74°–76° C.

One basic group (anhydrous medium): 100.3%.

Elemental analysis: found (C 54.49 H 6.60 N 21.02); calculated (C 54.11 H 6.81 N 21.04).

Sulfur (Schöniger): found 12.27: calculated 12.04.

IR Spectrum: characteristic bands at 2200 cm$^{-1}$ (C≡N st) and 1630 cm$^{-1}$ (C=N st).

EXAMPLE 3

N-cyano-N'-[2-[[[2-[(aminoiminomethyl)amino]-4-thiazolyl]methyl]thio]ethyl]formamidine maleate acid (R =

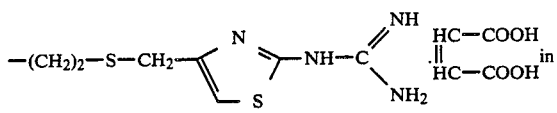

Formula I)

To a solution of 1.82 g of [4-[[(2-aminoethyl)thio]methyl]-2-thiazolyl]guanidine dihydrochloride (prepared according to U.S. Pat. No. 4,165,378) in 20 ml of water, are added 0.83 g of potassium carbonate. The resulting solution is evaporated under vacuum, and the obtained residue is treated with 20 ml of absolute ethanol. The insoluble solid is removed, and then 0.54 g of N-cyanoformimidate in 10 ml of ethanol are added dropwise onto the filtrate, under stirring and at room temperature. Stirring is maintained for 1 hour, after which the solvent is removed by underpressure distillation and the obtained residue is dissolved in 25 ml of acetone. Thereafter 1.4 g of maleic acid in 15 ml of acetone are added, resulting in a while solid which is then crystallized from methanol. 1.2 g are obtained of N-cyano-N'-[2-[[[2-[(aminoiminomethyl)amino]-4-thiazolyl]methyl]thio]ethyl]formamidine maleate acid.

Melting point: 178°–179° C.

One basic group (anhydrous medium): 99.9%.

Elemental analysis: found (C 39.12 H 4.61 N 23.89); calculated (C 39.09 H 4.29 N 24.55).

IR Spectrum: characteristic bands at 2190 cm$^{-1}$ (C≡N st) and 1615 cm$^{-1}$ (C=N st).

EXAMPLE 4

N-cyano-N'-[3-[3-(1-piperidinylmethyl)phenoxy]propyl]formamidine hydrochloride

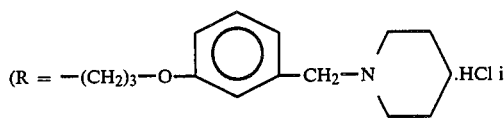

Formula I)

To a solution of 2.48 g of 3-[3-(1-piperidinylmethyl)phenoxy]-1-propanamine (prepared according to British Pat. No. 2,023,123 which is hereby incorporated by reference) in 25 ml of absolute ethanol, are added dropwise 0.98 g of ethyl N-cyano-formimidate in 15 ml of ethanol, under stirring and at room temperature. Stirring is maintained for 30 minutes, and then the ethanol is removed by underpressure distillation. An oil residue is formed, which is then dissolved in 250 ml of ethyl ether, after which 0.95 ml of 10N HCl/ethanol are added, yielding 1.4 g of N-cyano-N'-[3-[3-(1-piperidinylmethyl)phenoxy]propyl]formamidine hydrochloride.

Melting point: 57°61° C.

One basic group (anhydrous medium): 101.6%.

Elemental analysis: found (C 59.03 H 7.78 N 14.89); calculated (C 60.61 H 7.48 N 16.63).

Chlorides: found 10.52; calculated 10.84.

IR Spectrum: characteristic bands at 2190 cm$^{-1}$ (—C≡N st) and 1620 cm$^{-1}$ (—C=N st).

The blocking activity of histamine H$_2$-receptors was tested in Sprague-Dawley albino male rats weighing 350–450 g. Animals subject to 18-hour fasting were anaesthetized with urethane (1.5 g/kg i.p.), after which a longitudinal incision was performed on the abdominal wall, and pylorus and esophagus were cannulated for subject perfusion. In addition, femoral veins were cannulated for administration of test drugs and histamine solution.

The animals' stomachs were perfused with 1/8000N NaOH diluted solution at a rate of 2 ml/min. The perfusion liquid was then circulated through a 3 ml-volume chamber provided with a pH meter electrode. After calibrating the pH, histamine was perfused at 0.325 μmols/kg/min. The histamine perfusion caused a decrease of the perfusion liquid pH, which was inhibited by the compounds of the present invention.

The results, expressed as the inhibition rate of maximal pH decrease in relation to initial pH, have demonstrated that the compounds of the present invention N-cyano-N'-[2[[[2-[(aminoiminomethyl)amino]-4-thiazolyl]methyl]thio]ethyl]formamidine maleate acid (Example 3) and N-cyano-N'-[3-[3-(1-piperidinylmethyl)phenoxy]propyl]formamidine hydrochloride (Example 4) are, according to their ED$_{50}$ values (Table 1), 2.6 and 1.8 times more active respectively than Cimetidine.

TABLE 1

| Compound | ED$_{50}$ (μmols/kg) |
|---|---|
| From Example 3 | 2.17 |
| From Example 4 | 3.20 |
| Cimetidine | 5.60 |

Results of this nature with test animals generally indicate a similar behavior in humans.

These results demonstrate that the compounds according to the present invention inhibit histamine-induced gastric acid secretion. They are thus indicated for use in humans in the treatment of peptic ulcers and other pathologies caused or stimulated by gastric acidity.

The compounds of the present invention may, when mixed with pharmaceutically acceptable carriers, be administered by the oral route in the form of pills, tablets, capsules, dragees, lozenges, syrup, solution, and the like, by injections or rectally, at daily doses ranging from 5 to 2000 mg.

It will be understood that each of the elements described above, or two or more together, may also find a useful application in other types of pharmaceuticals differing from the types described above.

While the invention has been illustrated and described as embodied in N-Cyano-formamidines, process for making the same, and pharmaceutical preparations containing the same, it is not intended to be limited to the details shown, since various modifications and structural changes may be made without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed as new and desired to be protected by Letters Patent is set forth in the appended claims.

We claim:

1. A compound of the Formula (I)

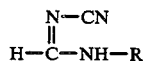

wherein R is 2[[(5-methyl-1H-imidazol-4-yl)methyl]thio]ethyl, 2-[[[5-[(dimethylamino)methyl]-2-furanyl]methyl]thio]ethyl, or 2-[[[2-[(aminoiminomethyl)amino]-4-thiazolyl]methyl]thio]ethyl, or a nontoxic acid addition salt thereof.

2. The compound according to claim 1, which is N-cyano-N'-2-[[(5-methyl-1H-imidazol-4-yl)methyl]thio]ethyl]formamidine dihydrochloride.

3. The compound according to claim 1, which is N-cyano-N'-[2-[[[5-[(dimethylamino)methyl]-2-furanyl]methyl]thio]ethyl]formamidine.

4. The compound according to claim 1, which is N-cyano-N'-[2-[[[2-[(aminoiminomethyl)amino]-4-thiazolyl]methyl]thio]ethyl]formamidine maleate acid.

5. The compound of the Formula (I) defined in claim 1 wherein R is 2-[[[2-[(aminoiminomethyl)amino]-4-thiazolyl]methyl]thio]ethyl or a nontoxic acid addition salt thereof.

* * * * *